United States Patent [19]

Sakurai et al.

[11] Patent Number: 5,412,072
[45] Date of Patent: May 2, 1995

[54] WATER SOLUBLE HIGH MOLECULAR WEIGHT POLYMERIZED DRUG PREPARATION

[75] Inventors: Yasuhisa Sakurai, Tokyo; Teruo Okano; Kazunori Kataoka, both of Chiba; Noriko Yamada, Tokyo; Shohei Inoue, Tokyo; Masayuki Yokoyama, Tokyo, all of Japan

[73] Assignee: Research Development Corp. of Japan, Tokyo, Japan

[21] Appl. No.: 496,741

[22] Filed: Mar. 21, 1990

[30] Foreign Application Priority Data

May 11, 1989 [JP] Japan ................................ 1-116082

[51] Int. Cl.$^6$ .............................................. C07K 9/00
[52] U.S. Cl. ...................................... 530/322; 536/6.4
[58] Field of Search ................... 536/6.4, 500; 514/34; 424/78, 80, 81; 530/322

[56] References Cited

U.S. PATENT DOCUMENTS 4,701,521 10/1987 Ryser et al. ........................ 530/322

OTHER PUBLICATIONS

D. Deprez–De Campeneere, Cancer Chemother. Pharmacol, 2, 25–30 (1979).
Yokoyama et al., 1987, Die Makromoleculare Chemie: Rapid Comm. 8:431–35.
Yokoyama et al., 1989 Die Makromoleculare Chemie Macromolecular Chemistry & Physc. 190:2041–54.
Yokoyama et al., 1990, J. Controlled Release, 11:269–78.

Primary Examiner—Douglas W. Robinson
Assistant Examiner—Elli Peselev
Attorney, Agent, or Firm—Pennie & Edmonds

[57] ABSTRACT

This invention is a water-soluble high molecular polymerized drug comprising a water-soluble clock copolymer having a hydrophilic segment and a hydrophobic pharmacological-functioning segment to side chain of which a drug is bonded. The hydrophilic first segments of the present invention include polyethylene glycol, polysaccharides, polyacrylamide, and so on. The hydrophobic segments being attached to a drug include polyaspartic acid, polyglutamic acid, polylysine, or derivatives thereof. Drugs to be attached to the hydrophobic segment include anti-cancer drugs, drugs for central nerve, drugs for circulatory organs, and so on.

1 Claim, 3 Drawing Sheets

━━━ : polyethylene glycol

∧∧∧ : polyaspartic acid

● : adriamycin in 0.1M sodium acetate buffer (pH 4.5)

WATER SOLUBLE HIGH MOLECULAR WEIGHT POLYMERIZED DRUG PREPARATION

FIELD OF THE INVENTION

The present invention relates to a water-soluble high molecular polymerized drug comprising a water-soluble block copolymer having a hydrophilic segment and a hydrophobic pharmacological-functioning segment to side chain of which a drug is bonded. As used throughout this specification, the terms "high molecular" and "low molecular" are intended to mean "high molecular weight" and "low molecular weight," respectively.

BACKGROUND OF THE INVENTION

In the past, several attempts had been performed for coupling a low molecular chemical drug with a high molecule, in order to give desirable distribution of the drug in the body so as to increase a drug half-life in the body. However, high-molecular compounds used in these attempts were copolymers consisting of one component, or polymers in which two components were polymerized alternatively or randomly.

In the cases of polymers above described when amounts of carried drugs increase for improvement of their efficacy, their water-solubility decreases owing to the hydrophobic nature of the drugs. The task of the present invention is to provide a water-soluble drug which does not decrease its water-solubility even if amounts of carried drugs were increased.

The present inventors tried to develop a high molecular polymerized drug, in order to solve the problem of the conventional high molecular polymerized drug. As a result of their eager research, they introduced a drug selectively to a second segment of a block copolymer comprising a first segment and the second segment, to give it hydrophobic nature. They succeeded in preventing the decrease of water-solubility accompanied by introduction of a drug and in preventing precipitate formation, by means of micelle formation in which the second segment is the inner-core and the first segment the outer-shell. The high molecular polymerized drug developed by the present inventors possesses good water-solubility, as well as attains, as a drug, stability in an aqueous solution higher than its original drug by use of the micelle formation.

SUMMARY OF THE INVENTION

That is, the present invention encompasses:

(1) Water-soluble high molecular polymerized drug comprising water-soluble block copolymer having a hydrophilic segment and a hydrophobic pharmacological-functioning segment, to side chain of which a drug is attached.

(2) Water-soluble high molecular polymerized drug according to (1) above, which forms micelles wherein the pharmacological-functioning segment is the inner-core and the hydrophilic segment the outer-core.

(3) Water-soluble high molecular polymerized drug according to (1), wherein the drug is an anti-cancer drug.

(4) Water-soluble high molecular polymerized drug according to (1), wherein the anti-cancer drug is adriamycin.

(5) Water-soluble high molecular polymerized drug according to (1), wherein the block copolymer is represented by the formula I:

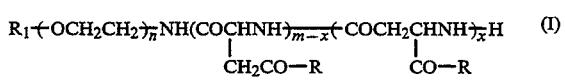

wherein R stands for OH, or

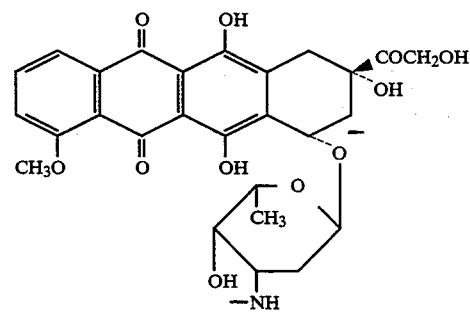

$R_1$ stands for —$CH_3$, —$CH_2CH_3$ or other alkyl group, n stands for an integer of from 5 to 400, m stands for an integer from 1 to 300, and x stands for an integer of from 0 to 300, whereupon at least one of R represents for

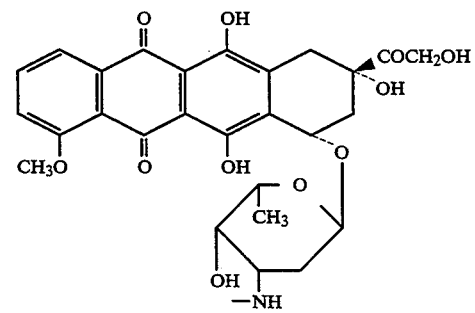

(6) Drug-bearing carrier, comprising a hydrophilic segment and a second segment which has a side chain capable of binding with a drug and turning hydrophobic upon binding with said drug.

(7) Drug-bearing carrier according to (6), which can be represented by the following formula II:

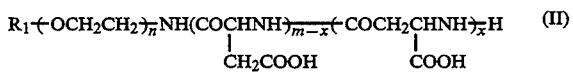

wherein $R_1$ stands for —$CH_3$, —$CH_2CH_3$ or other alkyl group, n stands for an integer of from 5 to 400, m stands for an integer of from 1 to 300, and x stands for an integer of from 0 to 300.

(8) Block copolymer represented by the following formula I:

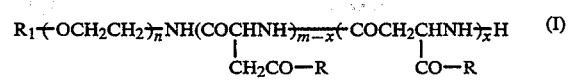

wherein R stands for OH or

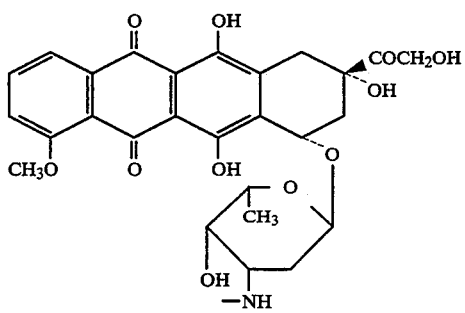

$R_1$ stands for —$CH_3$, —$CH_2CH_3$ or other alkyl group, n stands for an integer of from 5 to 400, m stands for an integer of from 1 to 300, x stands for an integer of from 0 to 300, and at least one of R stands for

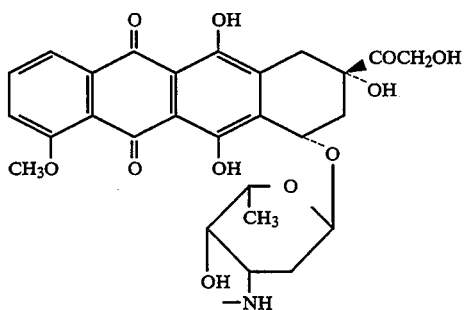

(9) Block copolymer represented by the following formula II:

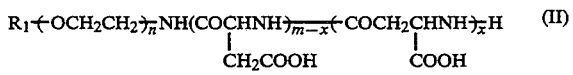

wherein R, stands for —$CH_3$, —$CH_2CH_3$ or other alkyl group, n stands for an integer of from 5 to 400, m stands for an integer of from 1 to 300, and x stands for an integer of from 0 to 300.

DETAILED DESCRIPTION OF THE INVENTION

For instance, the hydrophilic first segments of the present invention include polyethylene glycol, polysaccharides, polyacrylamide, polymethacrylamide, polyvinyl pyrrolidone, polyvinyl alcohols, polymethacrylates, polyacrylic esters, or polyamino acids or segments originated in derivatives thereof, and the second segments, which turn hydrophobic upon being attached to a drug, include ones having, in their side chain, polyaspartic acid, polyglutamic acid, polylysine, polyacrylic acid, polymethacrylic acid, polymalic acid, polylactic acid, polyalkylene oxide, or long-chain alcohols or segments originated in derivatives thereof.

Drugs to be attached to the second segment include, for example, anti-cancer drugs, such as adriamycin, daunomycin, methotrexate, mitomycin C as well as medical drugs, such as drugs for central nerve, drugs for peripheral nerve, drugs for allergy, drugs for circulatory organs, drugs for respiratory organs, drugs for digestive organs, hormone drugs, metabolizable medicines, antibiotics, and drugs for chemotherapy.

The present invention is described below in more detail, referring to an example of a copolymer comprising a segment originated in polyethylene glycol derivative and a segment originated in polyaspartic acid wherein an anti-cancer drug, adriamycin, is attached to the polyaspartic acid segment.

Figure 1:
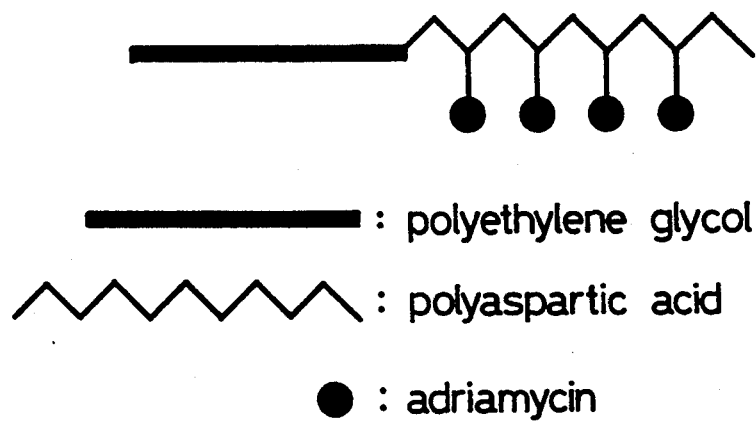
FIG. 1 shows the outline of the structure of the high molecular polymerized drug PEG-P (Asp(ADR)) of the present invention.
Figure 2:
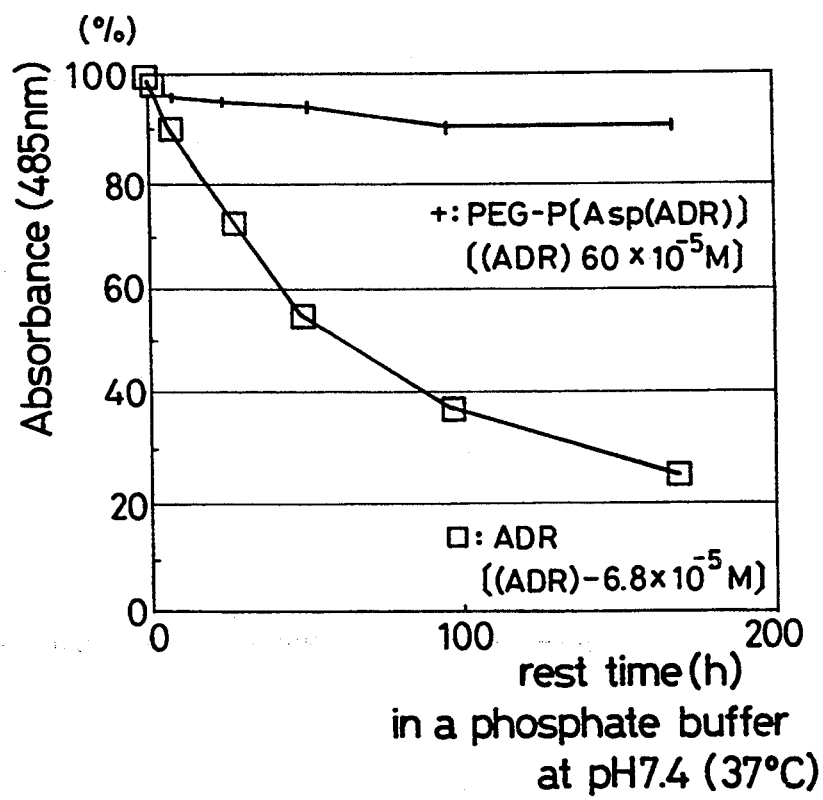
FIG. 2 shows change of absorbance at 485 nm, with time, of adriamycin (ADR) and of the high molecular polymerized drug preparation of PEG-P (Asp (ADR)) according to the present invention.

FIG. 1 shows the outline of the structure of a high molecular polymerized drug of the present invention, which is a block copolymer comprising two components namely, polyethylene glycol and polyaspartic acid wherein an anti-cancer drug, adriamycin, is bound to the carboxyl group in the side chain of the polyaspartic acid through an amide bond capable of being hydrolyzed in the body.

The synthesis of a high molecular polymerized drug, as shown in the reaction pathway below, is as follows: β-benzyl L-aspartate N-carboxy anhydride (BLA-NCA) was polymerized with an initiator of polyethylene glycol (M.W.: 250 to 18,000) having, at the terminal, an alkoxy group such as a methoxy group and having, at another terminal, a primary amino group, to prepare polyethylene glycol-poly (β-benzyl L-aspartate) block copolymer (PEG-PBLA), followed by subjecting the PEG-PBLA to alkali hydrolysis, to obtain a drug-bearing carrier of the present invention, i.e. polyethylene glycol-polyaspartic acid block copolymer (PEG-P(Asp)). Eighty % of the resultant PEG-P(Asp) received β-amidation on the hydrolysis. By adding adriamycin an anti-cancer drug and water-soluble carbodiimide (EDC) to the PEG-P(Asp), an amide bond was formed between primary amino group of the adriamycin and carboxyl group in the side chain of the polyaspartic acid segment, to obtain a high molecular polymerized PEG-P(Asp(ADR)).

Both the PEG-P(Asp) and PEG-P(Asp(ADR)) are novel ones as chemical substances.

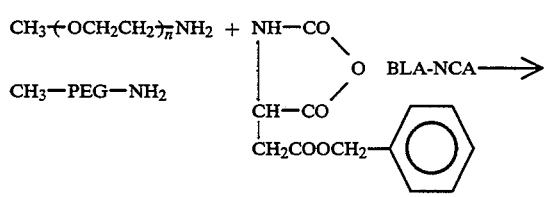

-continued $$CH_3(OCH_2CH_2)_n NH(COCHNH)_m H$$
$$|$$
$$CH_2COOCH_2\text{-Ph}$$

PEG—PBLA $$\downarrow$$

$$CH_3(OCH_2CH_2)_n NH(COCHNH)_{m-x}(COCH_2CHNH)_x H$$
$$|\qquad\qquad\qquad |$$
$$CH_2COOH\qquad\quad COOH$$

PEG—P(Asp)  (II)

$$\xrightarrow{\text{ADR}}_{\text{EDC}}$$

$$CH_3(OCH_2CH_2)_n NH(COCHNH)_{m-x}(COCH_2CHNH)_x H$$
$$|\qquad\qquad\qquad |$$
$$CH_2CO-R\qquad\quad CO-R$$

PEG—P[Asp(ADR)]  (I)

wherein R stands for OH or

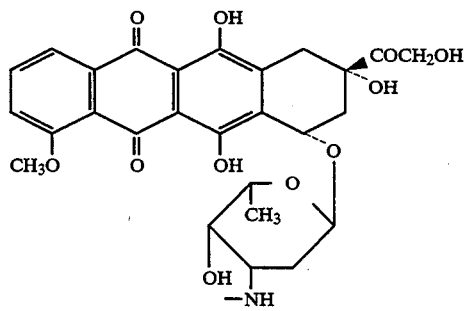

n stands for an integer of from 5 to 400, m stands for an integer of from 1 to 300, and x stands for an integer of from 0 to 300, whereupon at least one of R stands for

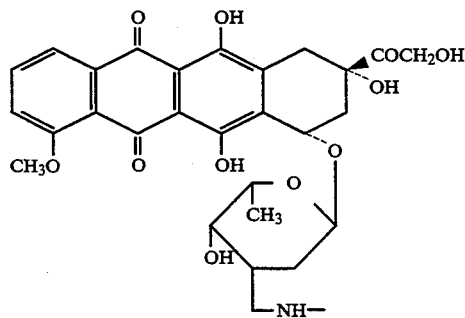

The molecular weight of the polyaspartic acids (P(Asp)) part is variable from 116 to 35,000. Substitution ratio of adriamycin (based on asparpartic acid residues) obtained was of 12 to 33 mol % in case a molecular weight of the P(Asp) is 1,900, and 3 to 37 mol % in case the molecular weight is 10,000.

The synthesized high molecular drug, despite the high adriamycin-substitution ratio, demonstrates good water-solubility, and keeps its water-solubility even when lyophilized or concentrated (calculated amounts: 20 mg of adriamycin/ml).

The high molecular polymerized drug possesses high stability as medicine as compared with the original adriamycin (ADR). In addition, the high molecular polymerized drug forms micelles in an aqueous solution. The sizes of the micelles are about 30 to 200 nm in diameter. It was revealed that an extremely severe condition of addition of a surface-active agent of SDS, is required to destroy the micelles, and thus the stability of the present high molecular micelles in water was proven. Furthermore, no change in the micelles-forming ability was recognized even by exposure to ultrasonic or by lyophilization.

As shown in Table 1, an anti-cancer activity of the synthesized polymerized high molecular chemical drug was higher than that of the original adriamycin. Furthermore, the high anti-cancer activity was achieved with side effect less than the original adriamycin.

The high-molecular polymerized drug according to the present invention possesses high stability as drug, as well as keeps good water-solubility with reduced side effect, even if amounts of drug carried are increased, so that the present invention could provide quite effective drugs.

EXAMPLES

Example 1

β-Benzyl L-aspartate N-carboxy anhydride (BLA-NCA, 7.21 g) was dissolved in 12 ml of N,N'-dimethylformamide (DMF), followed by addition of 60 ml of chloroform. 6.00 g of polyethylene glycol (M.W. 4,300) bearing, at one terminal, methoxy group and, at another terminal, amino group was dissolved in 60 ml of chloroform, and the solution was added to the BLA-NCA solution. After 70 hrs., the reaction mixture was dropped into 2 l of diethyl ether, and precipitated polymers were recovered by filtration, washed with diethyl ether, and dried in a vacuum, to obtain polyethylene glycol-poly (β-benzyl L-aspartate) block copolymer (PEG-PBLA). Yield was 10.09 g (84%).

10.03 g of PEG-PBLA was dissolved in 100 ml of chloroform. Alkaline solution, in which 0.43N sodium hydroxide was dissolved in a mixture (water:methanol: 1-propanol=1:1:2 (volume ratio)), was added to the PEG-PBLA. The alkali was 1.5 times equivalent to the benzyl ester part of the PBLA. After being stirred for 10 min. at 0° C., the mixture was dropped into 2 l of diethyl ether. Polymers precipitated were separated by filtration, dissolved in 20 ml of distilled water and dialyzed in water for 39 hrs, by use of Spectrapor 7 membrane (molecular weight cut-off=1,000). Then, the solution in the membrane was lyophilized to obtain polyethylene glycol-polyaspartic acid block copolymer (PEG-P(Asp)). Yield was 3.94 g (49%).

Proton NMR measurements showed the presence of 17 aspartic acid residues per block copolymer chain.

230.3 mg of the (PEG-P(Asp)) was dissolved in 1 ml of distilled water. 349.2 mg of adriamycin hydrochloride was dissolved in 260 ml of DMF, followed by addition of 1.3 times equivalent triethylamine. To the adriamycin solution was added the aqueous (PEG-P(Asp)) solution, and further 886 ml of water-soluble carbodiimide (EDC) was added. The mixture was stirred for 4 hrs. at 0° C. Then, another 886 ml of water-soluble carbodiimide was added and stirred for 19 hrs. at room temperature. By use of Spectrapor 7 membrane (molecular weight cut-off=1,000), the reaction mixture was dialyzed against 0.1M sodium acetate buffer (pH 4.5) for 3 hrs. After the dialysis, non-reacted adriamycin and other low molecular compounds were removed by ultrafiltration with Amicon YM30 membrane. Adriamycin contents in the resultant block copolymer of PEG-P(Asp(ADR)) were 31 mol % with respect to aspartic acid residues (from absorbance at 485 nm). In the same manner, the compound with a molecular weight of polyethylene glycol of 4,000 to 6,000 and 17 to 92 aspartic acid residues per block copolymer chain, and adriamycin contents of 9 to 37 mol % could be synthesized, all of which showed good water-solubility.

Example 2

Figure 3:
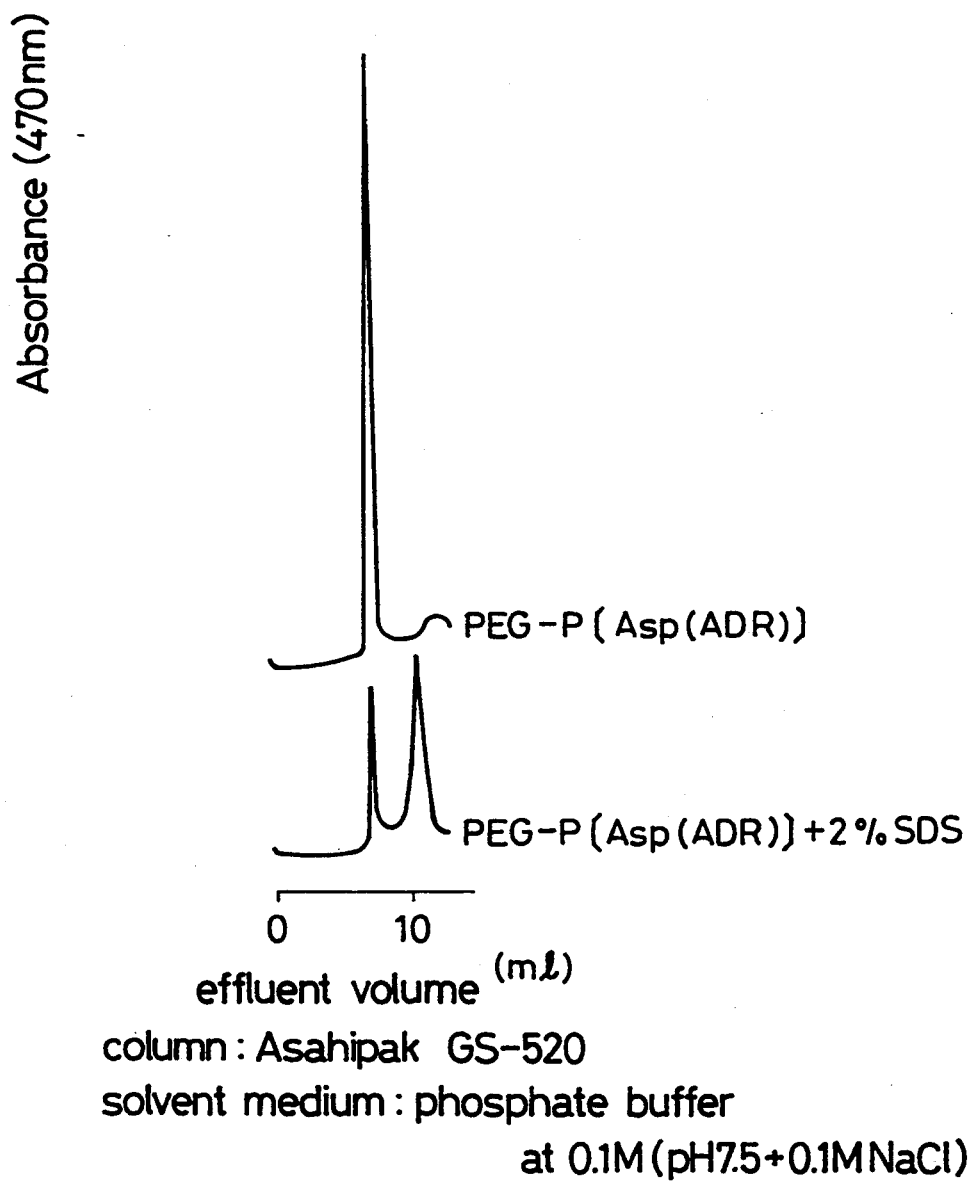
FIG. 3 shows analysis by gel-filtration HPLC, of the high molecular polymerized drug preparation PEG-P (Asp (ADR)) and of said preparation where a surface-active agent SDS was added.
Figure 4:
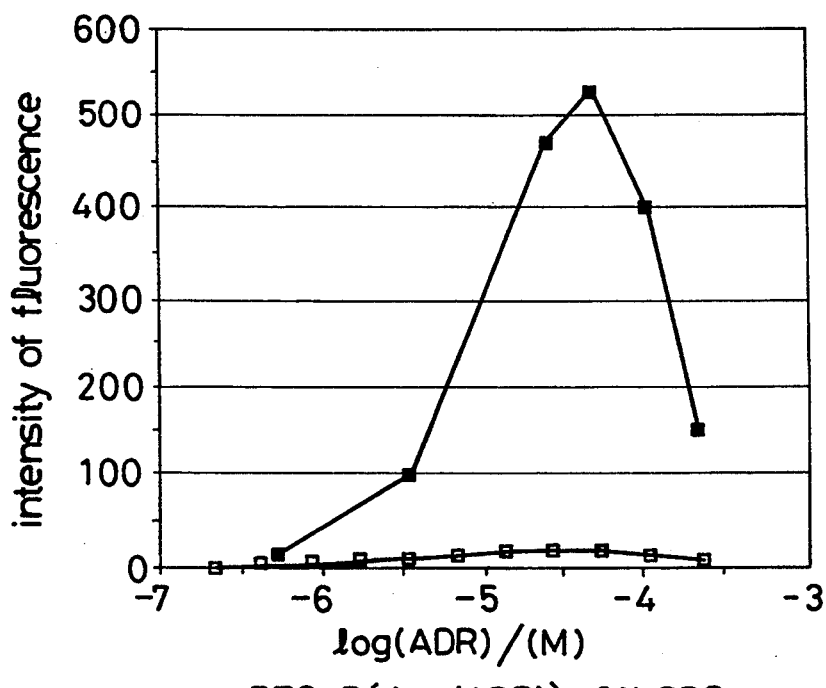
FIG. 4 shows results of fluorescence analysis of the high molecular polymerized drug preparation PEG-P(Asp(ADR)) and of said preparation where a surface-active agent SDS was added.
Figure 5:
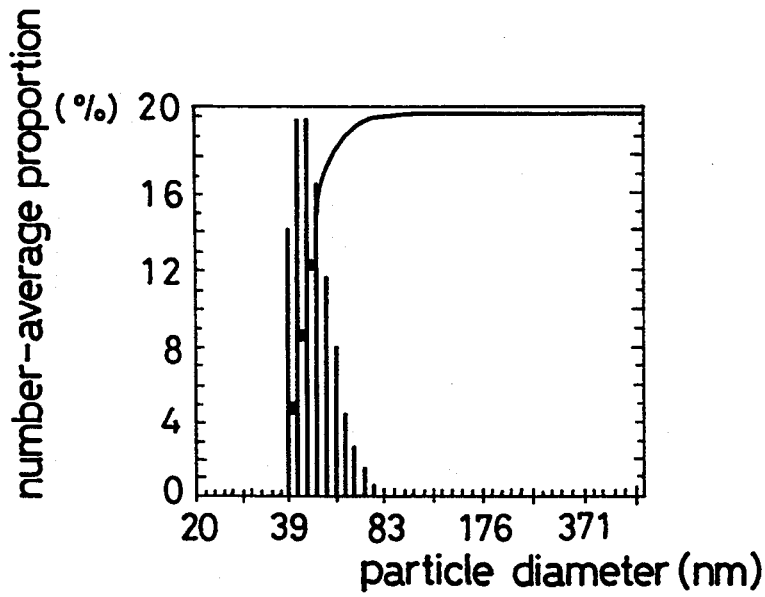
FIG. 5 shows distribution state of micelle diameter of the high molecular polymerized drug preparation of PEG-P (Asp(ADR)) of the present invention, by laser scattering measurement.

Laser scattering measurements showed that the micelles of PEG-P(Asp(ADR)) (with a molecular weight of PEG of 4,300, 17 aspartic acid residues per block copolymer chain, 31 mol % adriamycin) in an isotonic solution of phosphoric acid (pH 7.4) are 57 nm in weight-average diameter and 49 nm in number-average diameter (see FIG. 5). As shown in FIG. 3, the gel-filtration HPLC showed that most parts of the original peak move toward the side of small molecular weight by addition of a surface-active agent, sodium dodecyl sulfate (SDS), and that is, destruction of high-molecular micelles by the SDS was observed. The PEG-P(Asp(ADR)) of other proportions formed micelles from 30 to 80 nm in 5 diameter.

FIG. 3 shows absorbance change with time at 485 nm characteristic of adriamycin in a phosphate buffer at pH 7.4 (37° C.). Absorbance of adriamycin reduced to one-half within 100 hrs., whereas the synthesized high weight polymerized drug kept about 90% absorbance even after 168 hrs., to demonstrate that it is very stable.

Example 3

$10^6$ celles of P 388 mouse leukemia were intraperitoneally administered to female CDF1 mouse, and 24 hrs. after the administration, PEG-P(Asp(ADR)) (of the PEG with a molecular weight of 4,300, 17 aspartic acid residues per block copolymer chain and 31 mol % adriamycin) dissolved in physiological saline was intraperitoneally administered to the mouse. The ratio of survival days to that of controls (physiological saline was administered one day after administration of the leukemia cells) and body weight change were measured. Six mice were one group. Results are shown in Table 1. Adriamycin (ADR) showed that the maximum of T/C was 381%, whereas the high molecular polymerized drug demonstrated that it was 490% or higher, by a calculated amount of 200 mg of ADR/kg. In addition, ADR showed that, by the amount where 381% T/C was obtained, decrease of body weight (which indicates the degree of its side effect) was 12.5%, whereas the high molecular polymerized drug showed that it was only 7.4% at the maximum of T/C. From these observations, it was found that the synthesized high molecular chemical drug demonstrated higher anti-tumor activity with less side effect as compared with ADR.

TABLE 1

| Anti-tumor activity against P 388 mouse leukemia | | | | |
|---|---|---|---|---|
| Sample | Administered amount (mg/kg) | Median survival day | TC (%) | Change of body weight (5th day) |
| ADR | 7.5 | 15.3 | 191 | +4.4 |
| ADR | 15 | 30.5 | 381 | −12.5 |
| ADR | 30 | 6.5 | 81 | −17.1 |
| PEG-P (Asp(ADR)) | 80 | 18.0 | 225 | +6.1 |
| PEG-P (Asp(ADR)) | 120 | 32.5 | 382 | −5.5 |
| PEG-P (Asp(ADR)) | 200 | >42.0 | >490 | −7.4 |
| 1) Control: 8.0 ~ 8.6 days | | | | |

What is claimed is:

1. A compound of formula I:

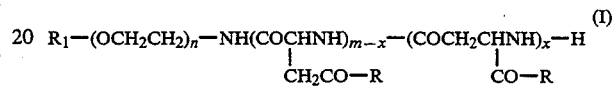

wherein R represents OH; or

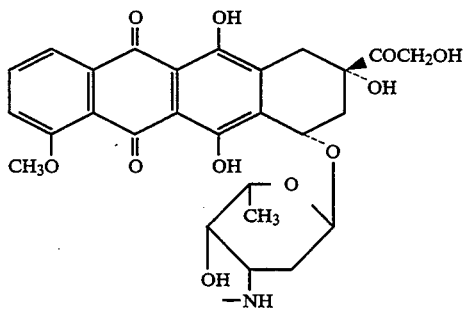

$R_1$ represents —$CH_3$ or —$CH_2CH_3$
n represents an integer from 90 to 400,
m represents an integer from 1 to 300,
x represents an integer from 0 to 300; and in which at least one R represents,

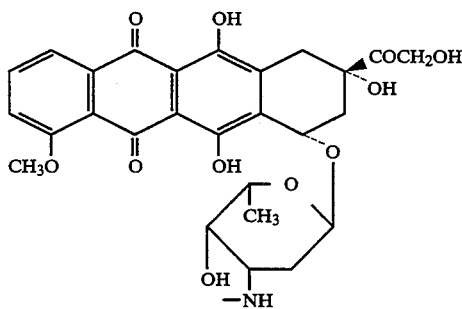

said compound forming a micelle when in an aqueous solution.

* * * * *